US012661070B2

(12) United States Patent
Mitchell et al.

(10) Patent No.: US 12,661,070 B2
(45) Date of Patent: Jun. 23, 2026

(54) MACHINE LEARNING TECHNIQUES FOR ESTIMATING CAROTID-FEMORAL PULSE WAVE VELOCITY AND/OR VASCULAR AGE FROM SINGLE-SITE ARTERIAL WAVEFORM MEASUREMENTS

(71) Applicant: Cardiovascular Engineering, Inc., Norwood, MA (US)

(72) Inventors: Gary F. Mitchell, Dover, MA (US); John D. Gotal, Framingham, MA (US)

(73) Assignee: Cardiovascular Engineering, Inc., Needham, MA (US)

( * ) Notice: Subject to any disclaimer, the term of this patent is extended or adjusted under 35 U.S.C. 154(b) by 399 days.

(21) Appl. No.: 18/133,434

(22) Filed: Apr. 11, 2023

(65) Prior Publication Data

US 2023/0371827 A1    Nov. 23, 2023

Related U.S. Application Data

(60) Provisional application No. 63/343,377, filed on May 18, 2022.

(51) Int. Cl.
| | |
|---|---|
| *A61B 5/02* | (2006.01) |
| *A61B 5/00* | (2006.01) |
| *A61B 5/021* | (2006.01) |
| *G16H 50/30* | (2018.01) |

(52) U.S. Cl.
CPC ........ *A61B 5/7264* (2013.01); *A61B 5/02007* (2013.01); *A61B 5/02125* (2013.01); *G16H 50/30* (2018.01)

(58) Field of Classification Search
None
See application file for complete search history.

(56) References Cited

U.S. PATENT DOCUMENTS

| | | |
|---|---|---|
| 2013/0310700 A1 | 11/2013 | Wiard et al. |
| 2014/0187883 A1 | 7/2014 | Lisogurski |
| 2016/0089042 A1 | 3/2016 | Saponas et al. |

(Continued)

OTHER PUBLICATIONS

Bahloul et al., A multilayer perceptron-based carotid-to-femoral pulse wave velocity estimation using PPG signal. 2021 IEEE EMBS International Conference on Biomedical and Health Informatics (BHI). Jul. 2021. 6 pages.

(Continued)

*Primary Examiner* — Meredith Weare
(74) *Attorney, Agent, or Firm* — Wolf, Greenfield & Sacks, P.C.

(57) ABSTRACT

Machine learning techniques for estimating an indication of carotid-femoral pulse wave velocity (CFPWV) and/or vascular age (VA) of a subject from an arterial waveform previously measured at a single site by an arterial waveform acquisition device coupled to the subject, the method comprising using at least one computer hardware processor to perform: obtaining the arterial waveform, the arterial waveform comprising a plurality of portions corresponding to a respective plurality of heartbeats of the subject; generating a representative heartbeat waveform from the arterial waveform; and providing the representative heartbeat waveform as input to a trained machine learning model to produce a corresponding output indicative of the CFPWV of the subject.

20 Claims, 11 Drawing Sheets

(56)                References Cited

U.S. PATENT DOCUMENTS

| | | |
|---|---|---|
| 2017/0014032 A1 | 1/2017 | Khair |
| 2018/0177459 A1 | 6/2018 | Eletr et al. |
| 2019/0076034 A1 | 3/2019 | Mori et al. |
| 2025/0169700 A1* | 5/2025 | Mitchell ............ A61B 5/02007 |

OTHER PUBLICATIONS

Baldo et al., Carotid-femoral pulse wave velocity in a healthy adult sample: The ELSA-Brasil study. International journal of cardiology. Jan. 15, 2018;251:90-5.

Dall'Olio et al., Prediction of vascular aging based on smartphone acquired PPG signals. Scientific reports. Nov. 12, 2020;10(1):19756. 10 pages.

Jin et al., Estimating pulse wave velocity from the radial pressure wave using machine learning algorithms. Plos One. Jun. 28, 2021;16(6):e0245026. 16 pages.

Jin, Cardiovascular function assessment using computational blood flow modelling and machine learning. Doctoral dissertation. King's College London. Apr. 2021. 232 pages.

Mejia-Mejia et al., Photoplethysmography signal processing and synthesis. Photoplethysmography. Elsevier. 2021. 52 pages.

Mitchell et al., Vascular age assessed from an uncalibrated, noninvasive pressure waveform by using a deep learning approach: the AI-VascularAge model. Hypertension. Jan. 2024;81(1):193-201. Author Manuscript. 19 pages.

Mitchell, Arterial stiffness in aging: Does it have a place in clinical practice? Recent advances in hypertension. Hypertension. Mar. 3, 2021;77(3):768-80.

Saugel et al., Cardiac output estimation using pulse wave analysis—physiology, algorithms, and technologies: a narrative review. British journal of anaesthesia. Jan. 1, 2021;126(1):67-76.

Agbaje et al., Effect of arterial stiffness and carotid intima-media thickness progression on the risk of dysglycemia, insulin resistance, and dyslipidemia: a temporal causal longitudinal study. Hypertension. Mar. 2022;79(3):667-78.

Agbaje et al., Effects of arterial stiffness and carotid intima-media thickness progression on the risk of overweight/obesity and elevated blood pressure/hypertension: a cross-lagged cohort study. Hypertension. Jan. 2022;79(1):159-69.

Avolio et al., Arterial blood pressure measurement and pulse wave analysis-their role in enhancing cardiovascular assessment. Physiological measurement. Nov. 26, 2009;31(1):R1.

Ben-Shlomo et al., Aortic pulse wave velocity improves cardiovascular event prediction: an individual participant meta-analysis of prospective observational data from 17,635 subjects. Journal of the American College of Cardiology. Feb. 25, 2014;63(7):636-46.

Bikia et al., Leveraging the potential of machine learning for assessing vascular ageing: state- of-the-art and future research. European Heart Journal-Digital Health. Dec. 1, 2021;2(4):676-90.

Boutouyrie et al., Arterial stiffness and cardiovascular risk in hypertension. Circulation research. Apr. 2, 2021;128(7):864-86.

Cohen et al., Arterial stiffness and diabetes risk in Framingham Heart Study and UK Biobank. Circulation research. Sep. 2, 2022;131(6):545-54.

Frankel et al., Resistin, adiponectin, and risk of heart failure: the Framingham offspring study. Journal of the American College of Cardiology. Mar. 3, 2009;53(9):754-62.

Harris et al., Age, gene/environment susceptibility—Reykjavik Study: multidisciplinary applied phenomics. American journal of epidemiology. Author Manuscript. Available in PMC Aug. 10, 2009 (Published in final edited form as Am J Epidemiol. May 1, 2007; 165(9): 1076-1087). 21 pages.

Huttunen et al., Deep learning for prediction of cardiac indices from photoplethysmographic waveform: a virtual database approach. International Journal for Numerical Methods in Biomedical Engineering. Mar. 2020;36(3):e3303. 17 pages.

Kaess et al., Aortic stiffness, blood pressure progression, and incident hypertension. Jama. Sep. 5, 2012;308(9):875-81.

Kannel et al., An investigation of coronary heart disease in families: the Framingham Offspring Study. American journal of epidemiology, historical article (Sep. 1, 1979;110(3):281-90). Jun. 1, 2017;185(11).

Kotchen, Historical trends and milestones in hypertension research: a model of the process of translational research. Hypertension. Oct. 2011;58(4):522-38.

Li et al., Gradient Descent with Early Stopping is Provably Robust to Label Noise for Overparameterized Neural Networks. arXiv preprint arXiv:1903.11680. Jul. 3, 2019. 37 pages.

Mitchell et al., Arterial stiffness and cardiovascular events: the Framingham Heart Study. Circulation. Feb. 2, 2010;121(4):505-11.

Mitchell et al., Hemodynamic correlates of blood pressure across the adult spectrum: noninvasive evaluation in the Framingham Heart Study. Circulation. Oct. 5, 2010;122(14):1379-86.

Mitchell, Aortic stiffness, pressure and flow pulsatility, and target organ damage. Journal of applied physiology. Dec. 1, 2018;125(12):1871-80.

Quan et al., The sleep heart health study: design, rationale, and methods. Sleep. Dec. 1, 1997;20(12):1077-85.

Rolnick et al., Deep learning is robust to massive label noise. arXiv preprint arXiv:1705.10694. Feb. 26, 2018. 10 pages.

Shin et al., Photoplethysmogram based vascular aging assessment using the deep convolutional neural network. Scientific Reports. Jul. 5, 2022;12(1):11377. 10 pages.

Splansky et al., The third generation cohort of the National Heart, Lung, and Blood Institute's Framingham Heart Study: design, recruitment, and initial examination. American journal of epidemiology. Jun. 1, 2007;165(11):1328-35.

Sturlaugsdottir et al., Prevalence and determinants of carotid plaque in the cross-sectional REFINE-Reykjavik study. BMJ open. Nov. 1, 2016;6(11):e012457. 10 pages.

Vasan et al., Arterial stiffness and long-term risk of health outcomes: the Framingham Heart Study. Hypertension. May 2022;79(5):1045-56.

Westerhof et al., Normalized input impedance and arterial decay time over heart period are independent of animal size. American Journal of Physiology—Regulatory, Integrative and Comparative Physiology. Jul. 1, 1991;261(1):R126-33.

Hossain et al., Derivation and validation of gray-box models to estimate noninvasive in-vivo percentage glycated hemoglobin using digital vol. pulse waveform. Scientific reports. Jun. 9, 2021;11(1):12169.

Kagiyama et al., Machine learning assessment of left ventricular diastolic function based on electrocardiogramnal of the American College of Cardiology. Aug. 25, 2020;76(8):930-41.

Song et al., Serum cystatin C is related to pulse wave velocity even in subjects with normal serum creatinine. Hypertension Research. Oct. 2008;31(10):1895-902.

* cited by examiner

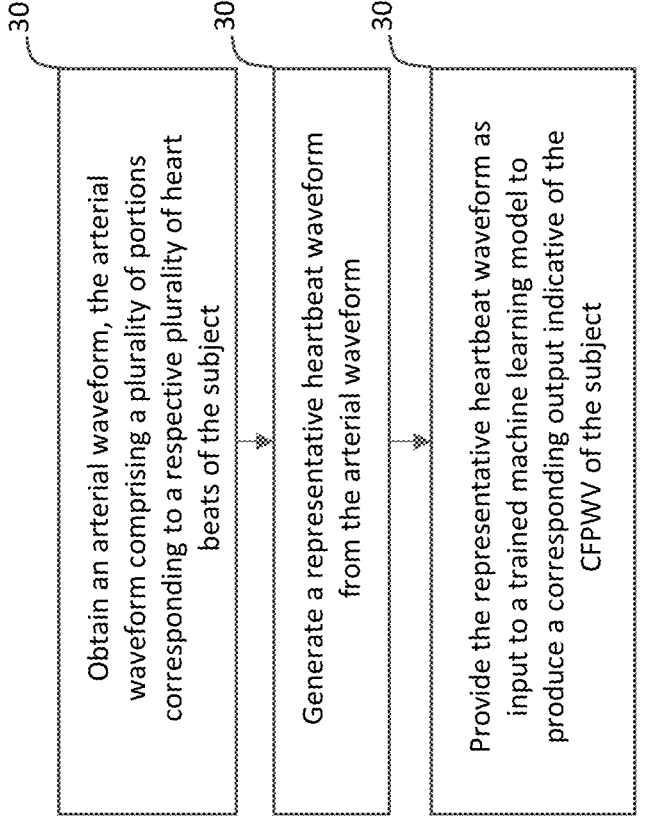

302

Obtain an arterial waveform, the arterial waveform comprising a plurality of portions corresponding to a respective plurality of heart beats of the subject

304

Generate a representative heartbeat waveform from the arterial waveform

306

Provide the representative heartbeat waveform as input to a trained machine learning model to produce a corresponding output indicative of the CFPWV of the subject

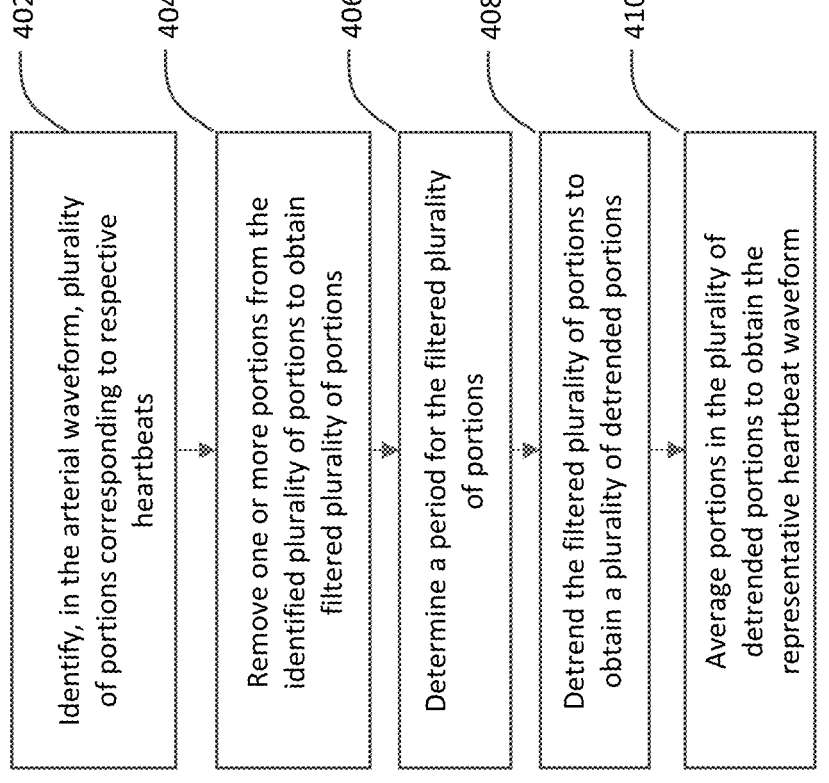

402

Identify, in the arterial waveform, plurality of portions corresponding to respective heartbeats

404

Remove one or more portions from the identified plurality of portions to obtain filtered plurality of portions

406

Determine a period for the filtered plurality of portions

408

Detrend the filtered plurality of portions to obtain a plurality of detrended portions

410

Average portions in the plurality of detrended portions to obtain the representative heartbeat waveform

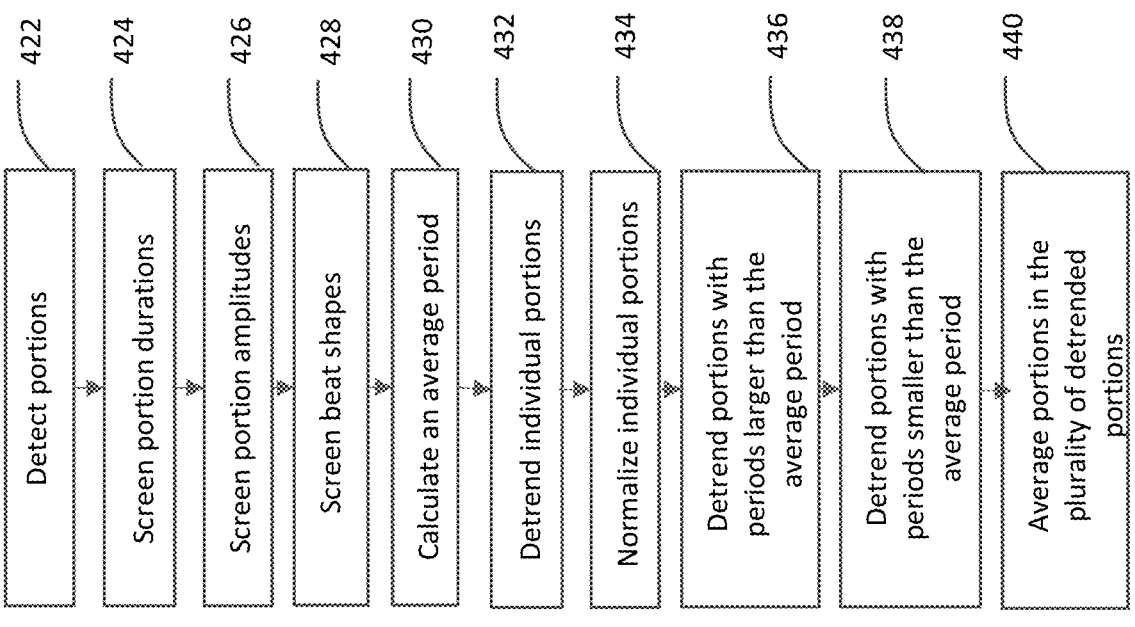

422 Detect portions

424 Screen portion durations

426 Screen portion amplitudes

428 Screen beat shapes

430 Calculate an average period

432 Detrend individual portions

434 Normalize individual portions

436 Detrend portions with periods larger than the average period

438 Detrend portions with periods smaller than the average period

440 Average portions in the plurality of detrended portions

420

MACHINE LEARNING TECHNIQUES FOR ESTIMATING CAROTID-FEMORAL PULSE WAVE VELOCITY AND/OR VASCULAR AGE FROM SINGLE-SITE ARTERIAL WAVEFORM MEASUREMENTS

CROSS-REFERENCE TO RELATED APPLICATIONS

This application claims the benefit of priority under 35 U.S.C. § 119(e) to U.S. Provisional Patent Application No. 63/343,377, filed May 18, 2022, and titled "MACHINE LEARNING TECHNIQUES FOR ESTIMATING CAROTID-FEMORAL PULSE WAVE VELOCITY AND/ OR VASCULAR AGE FROM SINGLE-SITE ARTERIAL WAVEFORM MEASUREMENTS", which is incorporated by reference herein in its entirety.

FIELD

The techniques described herein relate to estimating an indication of carotid-femoral pulse wave velocity (CFPWV) and/or vascular age (VA), and more particularly to machine learning techniques for estimating an indication of the CFPWV and/or VA of a subject from an arterial waveform previously measured at a single site by an arterial waveform acquisition device coupled to the subject.

BACKGROUND

Studies of the shape and timing of features of the arterial pulse have intrigued physiologists and physicians since ancient times. Persistent themes include the hypothesis that the volume, frequency and shape of the pulse waveform conveys important information regarding cardiovascular health.

Early work centered on subjective descriptions of pulse characteristics through palpation of various superficial arteries. A more quantitative analysis of the pulse waveform emerged in the mid-19th century with development of the sphygmometer by Heris son followed by the kymograph of Ludwig and the sphygmograph of Etienne Marey in the late 1800's. Mahomed subsequently modified the Marey sphygmograph to include the ability to assess the pressure required to occlude the arterial pulse, which was followed by development of the modern cuff-based sphygmomanometer and a shift in focus to the peak and trough only of the pressure waveform, reported as conventional systolic and diastolic blood pressure, which are well-known markers of cardiovascular disease risk. Ease of measurement and interpretation of cuff blood pressure led to loss of interest in pulse waveform characteristics until the mid-20th century, when a resurgence of interest in pulse waveform characteristic led to a proliferation of methods and devices that assess various potentially informative characteristic of the arterial pressure waveform.

Aortic stiffness may be used as a marker of vascular health and as a prognostic indicator for various adverse clinical outcomes. Carotid femoral pulse wave velocity (CFPWV), which is a reference standard measure of aortic stiffness, has been demonstrated to be a powerful indicator of risk for various adverse outcomes, including major cardiovascular disease events (e.g., myocardial infarction, heart failure, and stroke), chronic kidney disease, cognitive impairment and dementia. In addition, recent studies have shown that higher CFPWV is associated with subsequent development of high blood pressure, lipid abnormalities, obesity and diabetes, suggesting that CFPWV is involved at an early stage in the pathogenesis of cardiometabolic disease, underscoring the potential utility of CFPWV as a guide for targeted primordial prevention of cardiometabolic disease.

SUMMARY

Some embodiments provide for a method for using a machine learning model to estimate an indication of carotid-femoral pulse wave velocity (CFPWV) and/or vascular age (VA) of a subject from an arterial waveform previously measured at a single site by an arterial waveform acquisition device coupled to the subject. The method comprises using at least one computer hardware processor to perform: obtaining the arterial waveform, the arterial waveform comprising a plurality of portions corresponding to a respective plurality of heartbeats of the subject; generating a representative heartbeat waveform from the arterial waveform; and providing the representative heartbeat waveform as input to a trained machine learning model to produce a corresponding output indicative of the CFPWV of the subject.

Some embodiments provide for a system, comprising: at least one computer hardware processor; and at least one non-transitory computer-readable storage medium storing processor-executable instructions that, when executed by the at least one computer hardware processor, cause the at least one computer hardware processor to perform a method for using a machine learning model to estimate an indication of carotid-femoral pulse wave velocity (CFPWV) and/or vascular age (VA) of a subject from an arterial waveform previously measured at a single site by an arterial waveform acquisition device coupled to the subject. The method comprises: obtaining an arterial waveform, the arterial waveform comprising a plurality of portions corresponding to a respective plurality of heartbeats of a subject; generating a representative heartbeat waveform from the arterial waveform; and providing the representative heartbeat waveform as input to a trained machine learning model to produce a corresponding output indicative of the CFPWV of the subject.

Some embodiments provide for at least one non-transitory computer readable storage medium storing processor-executable instructions that, when executed by at least one computer hardware processor, cause the at least one computer hardware processor to perform a method for using a machine learning model to estimate an indication of carotid-femoral pulse wave velocity (CFPWV) and/or vascular age (VA) of a subject from an arterial waveform previously measured at a single site by an arterial waveform acquisition device coupled to the subject. The method comprises: obtaining the arterial waveform, the arterial waveform comprising a plurality of portions corresponding to a respective plurality of heartbeats of the subject; generating a representative heartbeat waveform from the arterial waveform; and providing the heartbeat waveform as input to a trained machine learning model to produce a corresponding output indicative of the CFPWV of the subject.

In some embodiments, the arterial waveform acquisition device comprises a tonometer. In some embodiments, the arterial waveform acquisition device comprises a wearable device. In some embodiments, the arterial waveform acquisition device comprises a plethysmographic (PG) device. The plethysmographic device may be a photoplethysmographic (PPG) device. In some embodiments, the arterial waveform acquisition device comprises an echocardiographic device. In some embodiments, the arterial waveform acquisition device comprises a digital blood pressure system. In some embodiments, the arterial waveform acquisition device comprises an electrical impedance sensor. In some embodiments, the arterial waveform acquisition device comprises an ultrasound imaging device.

In some embodiments, the arterial waveform comprises a pressure waveform or an arterial distension waveform. In some embodiments, the arterial waveform comprises an arterial flow waveform.

In some embodiments, the plurality of portions comprises at least 100, at least 250, at least 500, or at least 1000 portions corresponding to a respective plurality of heart beats.

In some embodiments, each portion of the plurality of portions comprises at least 500 or at least 1000 data points. In some embodiments, each portion of the plurality of portions comprises between 500 and 2000 data points.

In some embodiments, generating the heartbeat waveform from the arterial waveform comprises: identifying the plurality of portions in the arterial waveform; and determining the representative heartbeat waveform from the identified plurality of portions.

In some embodiments, determining the representative heartbeat waveform comprises averaging the identified plurality of portions to obtain the representative heartbeat waveform.

In some embodiments, the method further comprises: removing one or more portions from the identified plurality of portions to obtain a filtered plurality of portions, wherein determining the representative heartbeat waveform comprises averaging portions in the filtered plurality of portions to obtain the representative heartbeat waveform.

In some embodiments, the method further comprises: detrending one or more portions in the plurality of portions in the arterial waveform to obtain a plurality of detrended portions, wherein determining the representative heartbeat waveform comprises averaging portions in the plurality of detrended portions to obtain the representative heartbeat waveform.

In some embodiments, generating the heartbeat waveform from the arterial waveform comprises: identifying the plurality of portions in the arterial waveform; removing one or more portions from the identified plurality of portions to obtain a filtered plurality of portions; determining a period for the filtered plurality of portions; and detrending the filtered plurality of portions to obtain a plurality of detrended portions, wherein determining the representative heartbeat waveform comprises averaging portions in the plurality of detrended portions to obtain the representative heartbeat waveform.

In some embodiments, the method further comprises: determining one or more derivative waveforms of the representative heartbeat waveform; and providing the one or more derivative waveforms together with representative heartbeat waveform as the input to the trained machine learning model to produce the corresponding output indicative of the CFPWV of the subject.

In some embodiments, the trained machine learning model comprises a neural network model. In some embodiments, the neural network model comprises a convolutional neural network (CNN) model. In some embodiments, the CNN model comprises one or more convolutional layers, one or more rectified linear unit layers, one or more pooling layers, and one or more dropout layers. In some embodiments, the CNN model comprises at least 1 million or at least 5 million parameters. In some embodiments, the CNN model comprises between 1 and 20 million parameters. In some embodiments, the neural network model comprises a recurrent neural network model.

In some embodiments, the trained machine learning model comprises a regression model. In some embodiments, the regression model comprises a support vector machine (SVM) regression model. In some embodiments, the regression model comprises a random forest regression model.

In some embodiments, the method further comprises: predicting vascular age (VA) of the subject using a linear regression model different from the trained machine learning model and the output indicative of the CFPWV of the subject.

In some embodiments, the method further comprises: predicting aortic stiffness of the subject using the output indicative of the CFPWV of the subject.

In some embodiments, the method further comprises: predicting relative risk for myocardial infarction of the subject using the output indicative of the CFPWV of the subject.

In some embodiments, the method further comprises: predicting relative risk for heart failure of the subject using the output indicative of the CFPWV of the subject.

In some embodiments, the method further comprises: predicting relative risk for developing chronic kidney disease of the subject using the output indicative of the CFPWV of the subject.

In some embodiments, the method further comprises: predicting risk of the subject for developing any of hypertension, diabetes, obesity, myocardial infarction, heart failure, stroke, kidney disease, cognitive impairment and dementia using the output indicative of the CFPWV of the subject.

The foregoing is a non-limiting summary of the invention, which is defined by the attached claims.

BRIEF DESCRIPTION OF DRAWINGS

Various aspects and embodiments of the disclosure provided herein are described below with reference to the following figures. It should be appreciated that the figures are not necessarily drawn to scale. Items appearing in multiple figures are indicated by the same or a similar reference number in all the figures in which they appear.

FIG. 3 is a diagram of an illustrative process 300, which may be performed by any of systems 200A, 200B, and 200C, for estimating an indication of CFPWV and/or VA, in accordance with some embodiments of the technology described herein.

FIG. 4A is a diagram of an illustrative process 400 for generating a representative heartbeat waveform from an acquired arterial waveform, in accordance with some embodiments of the technology described herein.

FIG. 4B is a diagram of an illustrative process 420 for generating a representative heartbeat waveform from an acquired arterial waveform, in accordance with some embodiments of the technology described herein.

DETAILED DESCRIPTION

Figure 1:
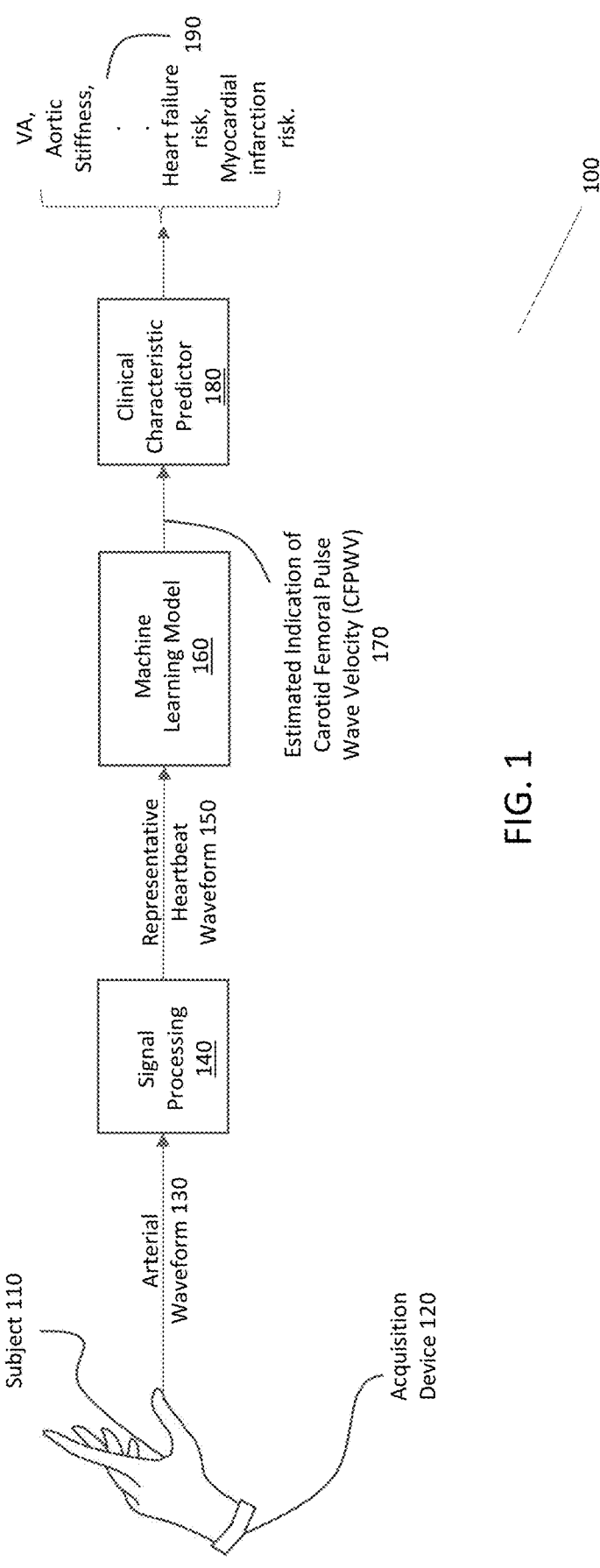
FIG. 1 is a diagram of an example process 100 for estimating an indication of CFPWV and/or VA, in accordance with some embodiments of the technology described herein.

As described above, carotid femoral pulse wave velocity (CFPWV)—a reference standard measure of aortic stiffness—has been demonstrated to be a powerful indicator of risk for various adverse outcomes. The inventors have appreciated that clinical application of stiffness measurements is limited by the need for specialized equipment and training required for proper measurement of CFPWV. The inventors have further appreciated that a method to robustly assess aortic stiffness from an easily accessible pressure waveform would offer the opportunity to capitalize on the clinical value of aortic stiffness assessment in a broad group, including self-assessment by individuals interested in evaluating effects of lifestyle modifications. Accordingly, the inventors have developed a machine learning model for assessing aortic stiffness (e.g., by predicting an indication of CFPWV) from various noninvasively recorded pulse waveforms.

In particular, the inventors have developed machine learning techniques for estimating an indication of CFPWV of a subject from an arterial waveform measured at a single site. In turn, the indication of CFPWV (which in some embodiments, may be an estimate of negative inverse CFPWV) may be used to generate a prediction of vascular age for the subject. In some embodiments, the techniques include using a machine learning model (e.g., a deep neural network model) to estimate a measure of carotid-femoral pulse wave velocity (CFPWV) by obtaining an arterial waveform (e.g., an arterial pressure waveform, an arterial distension waveform, or an arterial flow waveform) from a single site of the subject (e.g., using a tonometer or other device to measure the arterial waveform at the single site), the arterial waveform comprising a plurality of portions corresponding to a respective plurality of heartbeats of the subject, generating a representative heartbeat waveform from the arterial waveform, and providing the representative heartbeat waveform as input to a trained machine learning model to produce a corresponding output indicative of the CFPWV of the subject.

Conventional techniques for determining carotid femoral pulse wave velocity (CFPWV) require trained technicians to acquire pressure or flow waveforms in the carotid and femoral arteries using specialized equipment. The technicians then measure time delay (e.g., carotid-femoral transit time (CFTT)) between the upstrokes of the waveforms measured at the two sites (e.g., the carotid and femoral arteries in the neck and groin regions of the subject). The waveforms are acquired either simultaneously or together with a simultaneous electrocardiogram (ECG) so that relative time delay can be assessed. The carotid-femoral transit distance (CFTD) between the carotid and femoral sites is then measured and corrected for parallel transmission in the brachiocephalic artery and aorta by one of several potential approximations. Then the CFPWV is calculated using the transit distance and the time delay as CFPWV=CFTD/CFTT. Such conventional techniques require acquisition of multiple waveforms at multiple sites.

The inventors have appreciated that the above-described conventional approaches to determining carotid femoral pulse wave velocity (CFPWV) are limited in multiple respects. First, measuring subjects using tonometry is often uncomfortable, inconvenient, and time consuming. For example, in order to assess a subject's CFPWV, the subject is required to change into a hospital gown or other clothing that permits easy access to the carotid and femoral arteries in the neck and groin regions, respectively. ECG electrodes are placed on the chest or limbs and waveforms are acquired manually by trained technicians. Because of the time required for preparation, the acquisition generally requires ten to fifteen minutes of both technician and subject's time. In addition, conventional assessment of CFPWV requires access to the groin, which limits the conditions and locations in which measurement of the subject can be performed and raises privacy and patient comfort issues. Additionally, acquisition of reliable waveforms can be difficult in obese individuals.

Second, specialized equipment and trained technicians are also expensive and the subject has to be measured in person—the subject has to travel to where the technicians and the specialized equipment are located. Training to use the specialized equipment is necessary for technicians in order to enable them to use the equipment and interpret the measured data. With respect to interpretation, measured CFPWV values are also generally not well understood, making their measurement and analysis difficult. In sum, conventional techniques for determining CFPWV make it difficult to accurately determine the CFPWV of a subject. The inventors have recognized that it is desirable to be able to determine the CFPWV of a subject without specialized equipment, trained technicians, and in-person visits.

The inventors have developed new techniques for estimating CFPWV that address at least some (and, in some embodiments, all) of the above-described shortcomings of conventional techniques for determining carotid femoral pulse wave velocity. In particular, the inventors have developed machine learning based techniques for estimating CFPWV of a subject from an arterial waveform measured at a single site.

The machine learning techniques involve using a machine learning model (e.g., a deep learning model such as a deep neural network model) to process measurements made at a single site (e.g., carotid, brachial, or radial artery) in order to obtain an estimate of CFPWV. These machine learning techniques are able to obtain accurate estimates of CFPWV without requiring measurements to be obtained at multiple different sites by trained technicians (e.g., without concurrently obtaining tonometry measurements and ECG measurements). A single site recording from the carotid, brachial or radial artery takes only seconds (e.g., 20 seconds), rather than several minutes) and may be fully automated in most individuals (e.g., such a recording may be obtained by a wearable device, for example, a fitness tracker or a smartwatch). Because single site measurement is used, access to the groin of a subject is not necessary. This allows for subjects to be monitored at home and enables continuous monitoring of the subject over time. Continuous or intermittent monitoring gives hospitals and subjects access to more accurate information as well as information on changes over time, without then need for resources such as specialized equipment and trained technicians.

The machine learning techniques described herein also allow for estimation of vascular age, which facilitates interpretability of measurements. As described above, it may be difficult for all but the most trained health care providers to understand numerical values of predicted CFPWV, whereas it is substantially easier to understand a subject's vascular age (e.g., as compared to the subject's chronological age).

Accordingly, some embodiments provide a method for using a machine learning model to estimate an indication of carotid-femoral pulse wave velocity (CFPWV) and/or vascular age (VA) of a subject from an arterial waveform previously measured at a single site (e.g., from the carotid, brachial or radial artery) by an arterial waveform acquisition device coupled to the subject. The method comprises using at least one computer hardware processor to perform: (A) obtaining the arterial waveform, the arterial waveform comprising a plurality of portions corresponding to a respective plurality of heartbeats of the subject, (B) generating a representative heartbeat waveform from the arterial waveform (e.g., by identifying, filtering, pre-processing, and averaging the portions to obtain the representative heartbeat waveform); and (C) providing the representative heartbeat waveform as input to a trained machine learning model (e.g., a neural network, a support vector machine, or any other suitable non-linear regression model) to produce a corresponding output indicative of the CFPWV of the subject.

In some embodiments, the output indicative of the CFPWV may be an estimate of the CFPWV directly. In other embodiments, the output indicative of the CFPWV may or may be an estimate of another related quantity, such as, for example, the normalized negative inverse of CFPWV (nCFPWV) defined by −3/CFPWV. Predicting the nCFPWV (rather than directly predicting CFPWV) may be beneficial because nonlinearity and heteroskedasticity of CFPWV in native units may complicate the prediction of vascular age and may produce uninformative estimates. For example, if raw CFPWV, the relation would be markedly nonlinear and rapidly increasing after about 50 years of age and the standard deviation would also increase rapidly after 50 years of age (this is the heteroskedasticity). By contrast, predicting nCFPWV normalizes the distribution and and linearizes the age relation avoiding the non-linearity and heteroskedasticity issues with direct CFPWV predictions.

Any of numerous types of waveform acquisition devices may be used. Examples of waveform acquisition devices include, but are not limited to, a tonometer, a wearable device (e.g., a fitness tracker device, a smartwatch, etc.), a plethysmographic (PG) device, a photoplethysmographic (PPG) device, an echocardiographic device or any other type of ultrasound imaging device, a digital blood pressure system, and/or an electrical impedance sensor.

In some embodiments, the arterial waveform may be a pressure waveform or a surrogate for the pressure waveform such as, for example, an arterial distension waveform (the distension is being caused by the pressure) or an arterial flow waveform.

The arterial waveform may be of any suitable duration and may be recorded over the course of any suitable number of heartbeats. In some embodiments, the arterial recording may be recorded for at least 10 seconds, at least 15 seconds, at least 20 seconds, at least 25 seconds, at least 30 seconds, at least 35 seconds, at least 40 seconds, at least 50 seconds, at least 60 seconds, between 10 and 30 seconds, between 15 and 25 seconds, between 1 and 60 seconds or any other suitable range within these ranges.

As described above, the arterial waveform comprises multiple portions corresponding to respective heartbeats. In some embodiments, the arterial waveform may comprise at least 10, 25, 50, 100, 200, 250, 300, 400, 500, 750, or 1000 portions corresponding respectively to 10, 25, 50, 100, 200, 250, 300, 400, 500, 750, or 1000 heartbeats.

The number of datapoints in the arterial waveform depends, in part, on the type of device used to make the record and the sampling rate of that device. In some embodiments, each of the multiple portions comprises at least 50 datapoints, 100 datapoints, 250 datapoints, 500 datapoints, 750 datapoints, 1000 datapoints, 2500 datapoints, between 100 and 1000 datapoints, between 500 and 2000 datapoints, between 50 and 5000 datapoints or any other suitable range within these ranges.

In some embodiments, generating the heartbeat waveform from the arterial waveform comprises identifying the plurality of portions in the arterial waveform (e.g., by segmenting the arterial waveform into the plurality of portions), and determining the representative heartbeat waveform from the identified plurality of portions.

In some embodiments, determining the representative heartbeat waveform comprises averaging the identified plurality of portions to obtain the representative heartbeat waveform. The averaging may be unweighted or weighted (e.g., where some of the portions contribute to a greater degree to the representative waveform than other portions).

In some embodiments, prior to being averaged, one or more of the plurality of portions may be filtered out and/or otherwise processed (e.g., detrended). Accordingly, in some embodiments, determining the representative heartbeat waveform may further include removing one or more portions from the identified plurality of portions to obtain a filtered plurality of portions, and the representative heartbeat waveform may be determined by averaging those portions that remained after filtering. The filtering of portions may be performed based on various types of criteria. For example, a portion may be filtered out based on its duration, based on the amplitude of the waveform within the portion, and/or based on the shape of the waveform in the portion. Additionally, or alternatively, in some embodiments of the method, one or more of the portions in the plurality of portions is detrended and it is the filtered and detrended portions that are averaged to produce the representative heartbeat waveform.

Accordingly, in some embodiments, generating the heartbeat waveform from the arterial waveform comprises: identifying the plurality of portions in the arterial waveform; removing one or more portions from the identified plurality of portions to obtain a filtered plurality of portions; determining a period for the filtered plurality of portions; and detrending the filtered plurality of portions to obtain a plurality of detrended portions. In turn, the representative heartbeat waveform may be obtained by averaging portions in the plurality of detrended portions.

In some embodiments, in addition to providing the representative heartbeat waveform as input to the trained machine learning model to obtain an indication of CFPWV, one or more additional inputs may be provided to the trained machine learning model to obtain the indication of CFPWV. For example, one or more derivative waveforms of the representative heartbeat waveform may be determined and provided, together with representative heartbeat waveform, as the input to the trained machine learning model to produce the corresponding output indicative of the CFPWV of the subject. For example, the one or more derivative waveforms can be any combination of the representative heartbeat waveform (P), a derivative of the representative heartbeat waveform (dP), and/or a second derivative of the representative heartbeat waveform (d2P).

Any of numerous types of machine learning models may be used. In some embodiments, the trained neural network may include a neural network model. In some embodiments, the trained neural network model may be a recurrent neural network model. In some embodiments, the neural network model may be a convolutional neural network (CNN) model, which comprises one or more convolutional layers (e.g. at least 2, at least 4, at least 8, at least 16 layers), one or more rectified linear unit (ReLU) layers, one or more pooling layers, one or more dropout layers, and/or one or more fully connected layers. In some embodiments, the CNN model may have the illustrative architecture shown in FIG. 7.

Convolutional neural network models are complex models having a large number of parameters. For example, in some embodiments, the CNN model comprises at least 1 million parameters, at least 5 million parameters, at least 10 million parameters, at least 25 million parameters, at least 50 million parameters, between 1 and 20 million parameters, between 10 and 100 million parameters or any other range within these ranges.

It should be appreciated, however, that in other embodiments, one or more other types of machine learning models may be used. For example, a support vector machine (SVM) regression model may be used, a random forest regression model may be used, or any other suitable type of non-linear regression model may be used, as aspects of the technology described herein are not limited in this respect.

In some embodiments, the vascular age (VA) of the subject may be predicted based on the output indicative of the CFPWV of the subject. For example, a regression model may be used to estimate VA of the subject based on an estimate of nCFPWV of the subject.

Many other uses of the predicted indication of CFPWV are within the scope of the inventive subject matter disclosed herein. For example, the output indicative of the CFPWV of the subject may be used to predict aortic stiffness of the subject, to predict relative risk for myocardial infarction of the subject, to predict relative risk for heart failure of the subject, and/or to predict relative risk for developing chronic kidney disease of the subject. In some embodiments, the output indicative of the CFPWV may be used to predict risk of the subject for developing any of hypertension, diabetes, obesity, myocardial infarction, heart failure, stroke, kidney disease, cognitive impairment and dementia.

Following below are more detailed descriptions of various concepts related to, and embodiments of, estimating an indication of carotid femoral pulse wave velocity (CFPWV) and/or vascular age (VA) for a subject. It should be appreciated that various aspects described herein may be implemented in any of numerous ways. Examples of specific implementations are provided herein for illustrative purposes only. In addition, the various aspects described in the embodiments below may be used alone or in any combination and are not limited to the combinations explicitly described herein.

FIG. 1 is a diagram of an example process 100 for estimating an indication of CFPWV and/or VA, in accordance with some embodiments of the technology described herein. As shown in FIG. 1, process 100 includes using an acquisition device 120 to measure an arterial waveform 130 of a subject 110.

The acquisition device 120 may be any device suitable for measuring arterial waveforms. For example, the arterial waveform acquisition device 120 may be or may comprise a tonometer, a wearable device (e.g., a fitness tracker, a smartwatch), a plethysmographic (PG) device, a photoplethysmographic (PPG) device, an echocardiographic device, a digital blood pressure system, an electrical impedance sensor, and/or an ultrasound imaging device. Acquisition device 120 may be a combination of two or more of the foregoing types of acquisition devices.

In embodiments, it may be advantageous to use a wearable acquisition device 120. For example, a wearable sensor would offer the ability to acquire a continuous or intermittent assessment of values indicating CFPWV over time, for example, during activities of daily living. Changes in aortic stiffness during stress or activity may provide additional useful prognostic information.

The acquisition device 120 may be positioned to measure the arterial waveform 130 at a single site of a subject. For example, the acquisition device 120 may be configured to measure the arterial waveform 130 from the carotid, brachial or radial artery of the subject. The acquisition device 120 may be positioned at any suitable site for taking such measurements. In the context of wearables, the subject 110 may be wearing the acquisition device 120 on their arm, wrist, finger, fingertip, earlobe, etc.

In some embodiments, the arterial waveform 130 may be a pressure waveform or a surrogate thereof (e.g., a time-resolved arterial distension waveform or an arterial flow waveform). When the heart contracts, the left ventricle injects a quantity of blood into the aorta, which creates a forward traveling pressure and flow waveform. This forward traveling wave encounters numerous regions of impedance mismatch that lead to partial wave reflection. The resulting aggregate reflected wave is apparent in the aforementioned pressure waveforms. In addition, between heart beats, pressure in the aorta decays with a time constant that is proportional to the product of total compliance and resistance of the arterial system. The interplay of forward and reflected waves and rate of pressure decay interact to create the final complex features of the observed pressure waveform.

The arterial waveform 130 may include a plurality of portions where each particular portion may correspond to a respective heartbeat such that the particular portion was recorded in a time period associated to the respective heartbeat. The arterial waveform 130 may have any suitable number of portions (e.g., at least 10, 25, 50, 100, 200, 250, 300, 400, 500, 750, or 1000 portions corresponding respectively to 10, 25, 50, 100, 200, 250, 300, 400, 500, 750, or 1000 heartbeats). The arterial waveform 130 may be of any suitable duration (e.g., at least 10 seconds, at least 15 seconds, at least 20 seconds, at least 25 seconds, at least 30 seconds, at least 35 seconds, at least 40 seconds, at least 50 seconds, at least 60 seconds, between 10 and 30 seconds, between 15 and 25 seconds, between 1 and 60 seconds or any other suitable range within these ranges).

In some embodiments, arterial waveform 130 is obtained in a single continuous recording. In some embodiments, the arterial waveform 130 may comprises multiple continuous recordings made at distinct times.

Once arterial waveform 130 is acquired by the acquisition device 120, the waveform 130 is processed during signal processing 140. Various types of signal processing may be applied during signal processing 140. For example, the arterial waveform may be segmented into multiple portions each corresponding to a respective heartbeat, the portions may be filtered (e.g., to remove partial beats, motion artifact, irregular heartbeats, for example, due to arrhythmias) to improve signal quality, the remaining portions may be detrended, normalized, and combined (e.g., averaged, using either regular or weighted averaging) to generate a representative heartbeat waveform 150. Aspects of signal processing 140 are described herein including with reference to FIGS. 4A and 4B.

In turn, the representative heartbeat waveform 150 is provided as input to a trained machine learning model 160. One or more other inputs may be provided together with the representative heartbeat waveform 150 (e.g., one or more derivatives of the representative heartbeat waveform 150 such as the first or second derivative waveforms). The machine learning model may be a neural network (e.g., a convolutional neural network) and may process the inputs to generate an output value indicative of an estimated CFPWV 170. The output value may be a direct estimate of CFPWV in some embodiments. In other embodiments, the output value may be an estimate of nCFPWV or a vascular age (VA) value (the latter in the situation that the machine learning model is trained to predict the VA directly).

In some embodiments, the process 100 further includes inputting the value 170 to clinical characteristic predictor 180. The clinical characteristic predictor 180 may use the value to predict (e.g., using linear regression, logistic regression, survival analysis or other known relationships and formulas, etc.) clinical characteristics such as VA, aortic stiffness, heart failure risk, myocardial infarction risk, etc. According to some embodiments, output values indicative of CFPWV and/or VA, or other characteristics predicted may be used as a basis for recommending various lifestyle modifications or pharmacologic interventions. In addition, ongoing monitoring of the values may be used to assess the ongoing impact of the lifestyle modification or pharmacologic intervention.

As one example, in some embodiments, the machine learning model 160 may output an nCFPWV value, which may be used to predict VA by linear regression. For example, in some embodiments, regression may be performed in a large, community-based sample of individuals to establish the linear relation of nCFPWV(y) vs. age(x). This relation may then be transposed to obtain the linear relation of vascular age(y) vs. nCFPWV(x), which linear relation may be used to compute VA from the output value of nCFPWV.

It should be appreciated that process 100 may be performed by any suitable combination of devices. Illustrative systems for performing process 100 are shown in FIGS. 2A, 2B, and 2C.

Figure 2A:
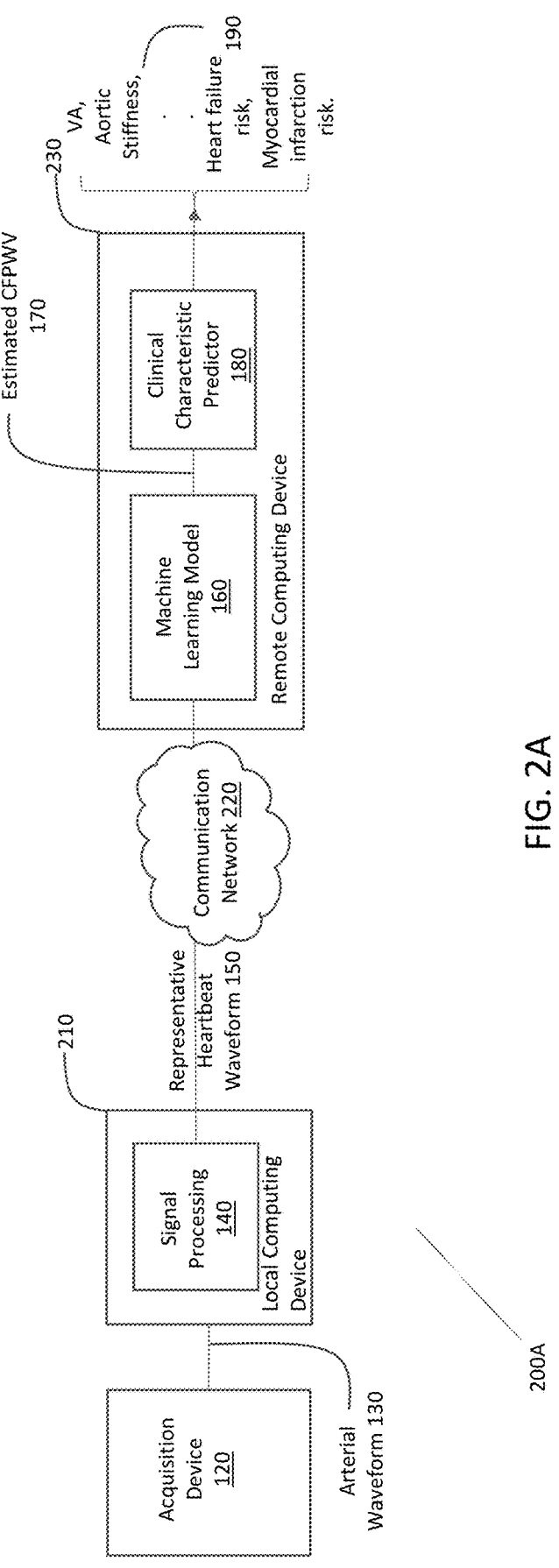
FIG. 2A is a diagram of an illustrative system 200A for estimating an indication of CFPWV and/or VA, in accordance with some embodiments of the technology described herein.
Figure 2B:
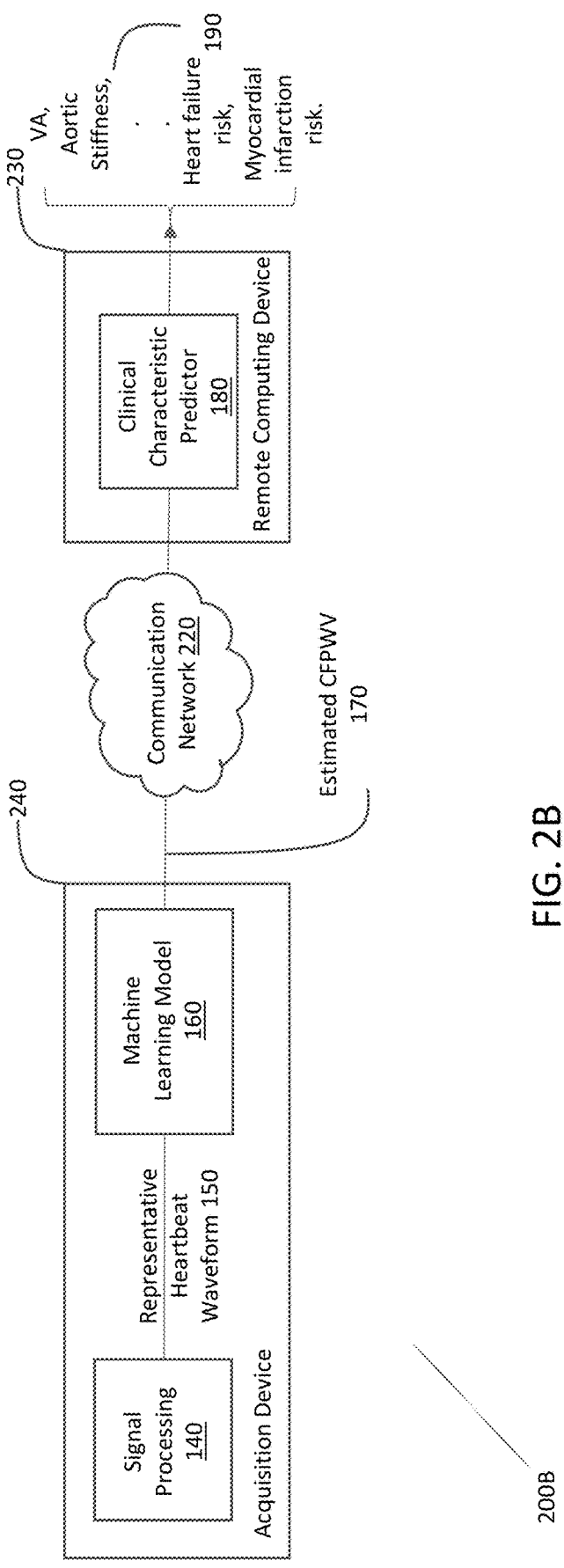
FIG. 2B is a diagram of an alternative illustrative system 200B for estimating an indication of CFPWV and/or VA, in accordance with some embodiments of the technology described herein.
Figure 2C:
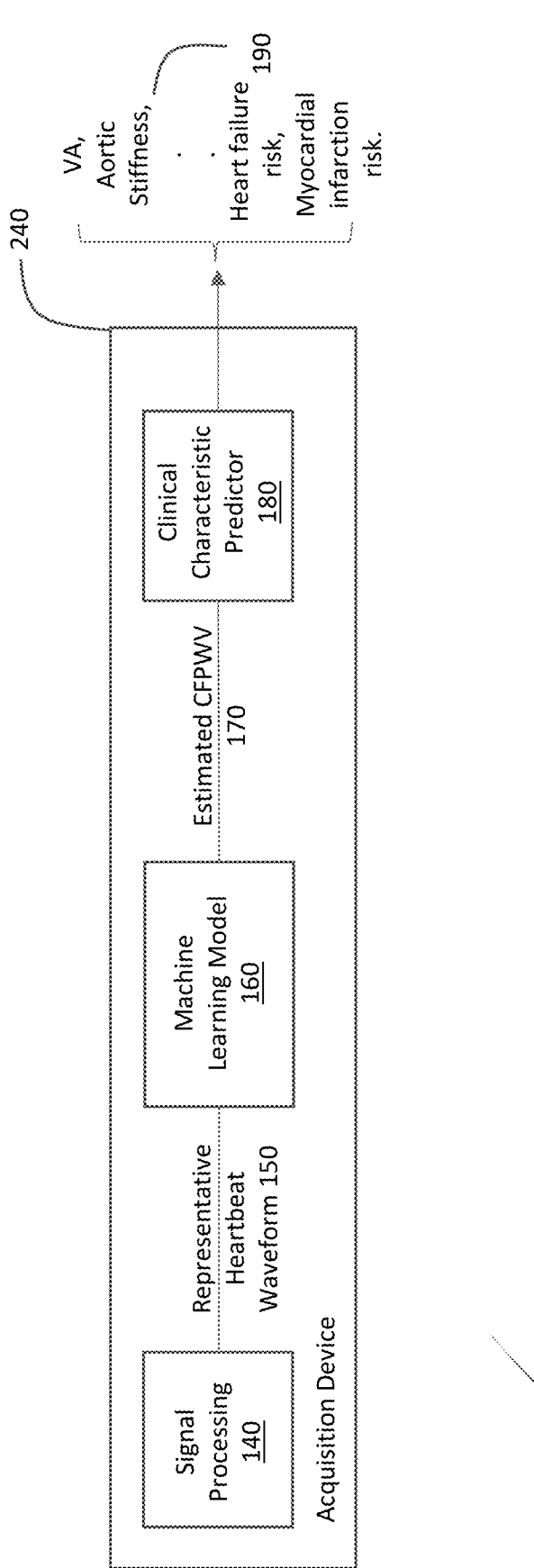
FIG. 2C is a diagram of an illustrative system 200C for estimating an indication CFPWV and/or VA, in accordance with some embodiments of the technology described herein.

As shown in FIG. 2A, system 200A includes acquisition device 120, local computing device 210 (separate from the acquisition device 120), communication network 220, and remote computing device 230. In system 200A, the local computing device 210 is be coupled to the remote computing device 230 via a communication network 220. Communication network 220 may be wired, wireless, Internet, mesh or any other suitable type of network, as aspects of the technology described herein are not limited in this respect. The local computing device 210 may be a smartphone, a tablet computer, a laptop computer, a desktop computer or any other suitable type of computing device. The remote computing device 230 may be a desktop computer, a rack-mounted computer, one or more devices used as part of a cloud-based computing environment or any other suitable type of computing device. In some embodiments, the local computing device 210 and/or the remote computing device 230 may have one or more graphical processing units (GPUs).

In this system, arterial waveform 130 generated by acquisition device 120 is provided (e.g., via a wired connection, a wireless connection, a network, or any suitable combination thereof) to local computing device 210. The waveform may be pushed from acquisition device 120 (e.g., proactively, without being requested) to local computing device 210 or may be pulled from acquisition device 120 (e.g., reactively, in response to a request to provide same). In turn, local computing device performs signal processing 140 on the received arterial waveform 130 to obtain representative heartbeat waveform 150 (and, optionally, one or more other features such as one or more derivative waveforms of the waveform 150), which is then transmitted, via communication network 220 to remote computing device 230. The remote computing device 230 may be configured to execute software for applying a trained machine learning model to inputs to obtain corresponding outputs and may, in this example, applying machine learning model 160 to the representative heartbeat waveform (and, optionally, one or more other features) to obtain an output value 170 indicative of an estimated CFPWV. Additionally, the remote computing device 230 may execute one or more clinical characteristics predictor 180 to determine other values 190 indicative of aortic stiffness or predicted risks.

One alternative to the system 200A shown in FIG. 2A is a system in which the acquisition device 120 and local computing device 210 are part of the same device. One such embodiment may be one in which a smartwatch or fitness tracker or other wearable device is configured to: (1) acquire an arterial waveform; and (2) perform one or more signal processing operations on the acquired arterial waveform.

Yet another variation is shown in FIG. 2B, which is a diagram of an alternative illustrative system 200B for estimating an indication of CFPWV and/or VA. System 200B includes acquisition device 240, which measures arterial waveform 130, performs signal processing 140 on the arterial waveform 130 to generate a representative heartbeat waveform 150 and provides that (together with one or more other inputs in some embodiments) as input to machine learning model 160 executing on acquisition device 240. The machine learning model 160 generates a value 170 indicative of an estimated CFPWV and provides it via communication network 220 to remote computing device 230 for further processing (e.g., to determine one or more other clinical characteristics). Such a variation may be used when a wearable device is configured to measure an arterial waveform, perform signal processing 140 to generate a representative arterial waveform, apply a trained machine learning model (e.g., a convolutional neural network) to process the representative arterial waveform to obtain an output value indicative of an estimated CFPWV.

Yet another variation is shown in FIG. 2C, where all processing is performed on a single computing device. Still other variations are possible and the variations illustrated in FIGS. 2A-2C are illustrative.

FIG. 3 is a diagram of an illustrative process 300, which may be performed by any of systems 200A, 200B, and 200C, for estimating an indication of CFPWV and/or VA, in accordance with some embodiments of the technology described herein.

Figure 5B:
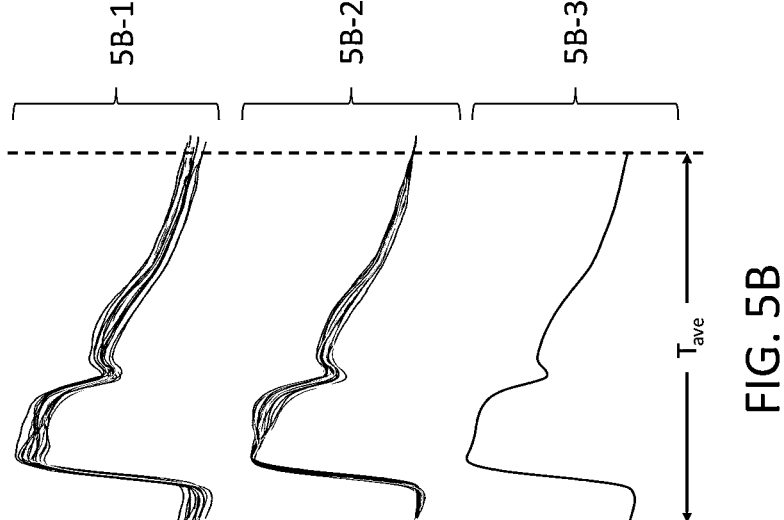
FIG. 5B shows multiple panels including: (i) panel 5B-1 that shows example identified portions of the acquired arterial waveform 500 of FIG. 5A, in accordance with some embodiments of the technology described herein; (ii) panel 5B-2 that shows a subset of the identified portions of the acquired arterial waveform shown in panel 5B-1, the subset being obtained by filtering the identified portions using one or more filtering criteria, in accordance with some embodiments of the technology described herein; and (iii) panel 5B-3 that shows a representative heartbeat waveform generated from the filtered portions of the acquired arterial waveform shown in panel 5B-2, in accordance with some embodiments of the technology described herein.
Figure 5A:
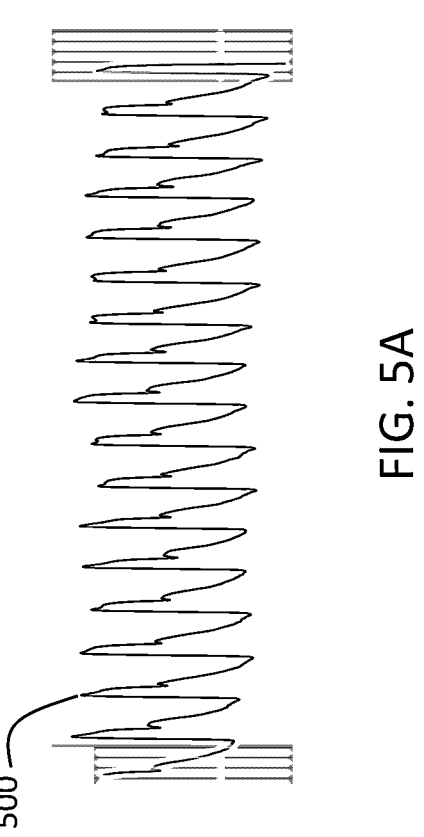
FIG. 5A is a graph of an example acquired arterial waveform, in accordance with some embodiments of the technology described herein.

Process 300 begins at act 302, where an arterial waveform is obtained. In some embodiments, the arterial waveform has been previously obtained by an acquisition device and is simply accessed at act 302. In other embodiments, the arterial waveform is acquired by an acquisition device as part of act 302. In some embodiments, the arterial waveform may be preconditioned using various low-pass or high-pass analog or digital filters by the acquisition device. The arterial waveform may comprise a plurality of portions corresponding to a respective plurality of heartbeats of the subject. Examples of duration of the arterial waveform, number of portions of the arterial waveform, and number of samples per portion of the arterial waveform are provided herein. As described herein, the arterial waveform may be an arterial pressure waveform or a surrogate thereof (e.g., an arterial distension waveform, or an arterial flow waveform). FIG. 5A shows an example of an arterial waveform.

Next, process 300 proceeds to act 304, where a representative heartbeat waveform is generated from the arterial waveform. In some embodiments, the representative heartbeat waveform may be generated by segmenting the arterial waveform into multiple portions, filtering the portions to remove one or more outliers, detrending the filtered portions, and averaging the detrended portions to obtain the representative heartbeat waveform. In some embodiments, various normalization steps may be applied. For example, the amplitude of the representative heartbeat waveform may be normalized. As another example, the temporal extent of the representative heartbeat waveform may be normalized (e.g., by padding or by interpolation or decimation to a fixed duration). In some embodiments, one or more derivative waveforms (e.g., first derivative, second derivative, etc.) of the representative heartbeat waveform may also be computed (and may be normalized or standardized). Aspects of generating a representative heartbeat waveform are described herein including with reference to FIGS. 4A, 4B, and 5B. An example of a representative heartbeat waveform is shown in panel 5B-3 of FIG. 5B.

Figure 7:
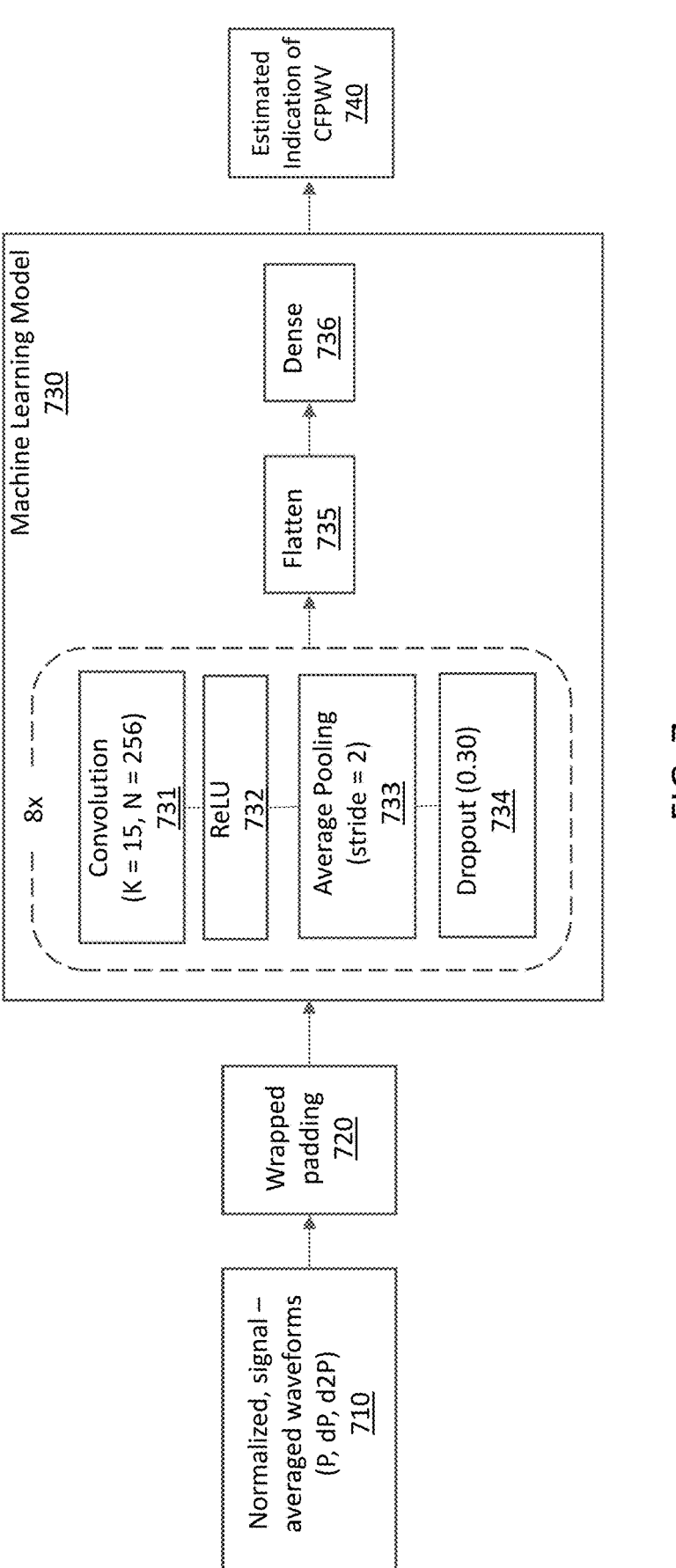
FIG. 7 is an example of a machine learning model 730 for estimating an indication of CFPWV and/or VA, according to some embodiments of the technology described herein.

Next, process 300 proceeds to act 306, where the representative heartbeat waveform generated at act 304 (and, optionally, one or more of its derivatives and/or one or more other features examples of which are described herein) is provided as input to a trained machine learning model (e.g., a trained convolutional neural network such as the CNN shown in FIG. 7) to produce a corresponding output indicative of the CFPWV of the subject. For example, the output may be a negative inverse CFPWV or a value indicative of VA. Optionally, the output generated at act 306 may be used to predict one or more other clinical characteristics of interest, examples of which are provided herein.

FIG. 4A is a flowchart of an illustrative process 400 for generating a representative heartbeat waveform from an acquired arterial waveform, in accordance with some embodiments of the technology described herein. Process 400 may be performed using any suitable computing device(s). For example, process 400 may be performed by an acquisition device (e.g., acquisition device 120 or 240), a local computing device co-located with the acquisition device (e.g., local computing device 210), or a compute device remote from the acquisition device (e.g., remote computing device 230).

Process 400 begins at act 402, which includes identifying, in the arterial waveform, a plurality of portions corresponding to respective heartbeats. This involves segmenting the arterial waveform into the plurality of portions, which may be done any suitable way. An example arterial waveform is shown in FIG. 5A and panel 5B-1 of FIG. 5B shows a graph of the plurality of waveform portions obtained by segmenting the arterial waveform.

In some embodiments, the segmentation may be performed by analyzing the arterial waveform itself. For example, one or more portions may be detected by analyzing the arterial waveform to identify the foot of the individual heartbeats in the waveform. A fiducial point may then be assigned (e.g., 100 ms) prior to each foot to ensure that subsequent detrending landmarks are prior to the steep upstroke of the foot. In turn, the locations and/or timing of the detected feet may be used to segment the arterial waveform into a plurality of portions corresponding to respective heartbeats. The "foot" of the arterial waveform may be identified in any suitable way. Let Pmax denote the maximum of the arterial waveform and dPmax denote the maximum of its first derivative. Then, as one example, the foot may be identified as the point at which the first derivative crosses 20% of the dPmax at a location that is prior to Pmax. As another example, the foot may be identified as the location of the local peak in the second derivative of the arterial waveform prior to the dPmax that is prior to Pmax.

As another example, peaks of the arterial waveform may be identified and used to segment the arterial waveform into portions corresponding to respective heartbeats.

In some embodiments, the segmentation may be performed by using auxiliary data derived from a source other than the arterial waveform itself. For example, if an ECG acquisition was performed concurrently with the acquisition of the arterial waveform, any of numerous standard QRS detectors known in the field of ECG may be used to identify individual heartbeats using the peak of the R-wave as a fiducial point. This fiducial point will typically occur 50 to 150 ms prior to the foot of the pressure waveform, depending on the location used to acquire the waveform.

The arterial waveform may be segmented into any suitable number of portions and this depends, in part, on the duration of the arterial waveform. Examples of arterial waveform duration and number of constituent portions are provided herein. Also, as described herein, in some embodiments, the plurality of portions may represent consecutive heartbeats measured during one continuous session (e.g., one 10-20 second reading from the acquisition device) or may comprise portions from multiple different sessions spanning different times of a day, a week, a month, etc.

Next, process 400 proceeds to act 404, which involves removing one or more portions from the identified plurality of portions to obtain a filtered plurality of portions. An example of the filtering is shown in FIG. 5B—panel 5B-2 shows a subset of the portions shown in panel 5B-1, the subset being obtained by the filtering performed at act 404 of process 400.

In some embodiments, the portions may be filtered based on their duration. For example, durations (e.g., cardiac period (T)) of the portions identified at act 402 may be assessed to filter out portions with excessively long or short durations, such as extra-systolic beats or beats with unusually long or short duration because of an underlying irregular rhythm such as atrial fibrillation. Thus, in some embodiments, one or more portions having a duration below a lower duration threshold may be filtered out. Additionally or alternatively, one or more portions having a duration above an upper duration threshold may be filtered out.

In some embodiments, the portions may be filtered based on their amplitudes. For example, each of the portions of the waveform can be screened for outliers that have unusually large or small amplitudes, suggesting a potential artifact. Thus, in some embodiments, one or more portions having at least one amplitude below a lower amplitude threshold may be filtered out. Additionally or alternatively, one or more portions having at least one amplitude above an upper amplitude threshold may be filtered out.

In some embodiments, the portions may be filtered based on the shapes of the waveform in each portion. In this way, irregularly-shaped portions having unusual morphology may be filtered out at act 404. This may be done in any suitable way. For example, in some embodiments, a portion of the plurality of portions corresponding to a median portion (e.g., a single beat waveform) can be computed by taking the median value at each timestep of the array of each of the plurality of portions that are identified (e.g., all portions identified at act 402, or a filtered subset thereof upon being filtered based on amplitude and/or duration criteria). The mean-squared deviation of each individual beat from this prototypical median portion can then be used as a criterion for rejecting portions that are sufficiently dissimilar from the others (e.g., when the mean-squared deviation or any other suitable distance measure of a particular portion is greater than a threshold, that particular portion may be filtered out).

Next, at act 406, the process 400 includes determining a period for the filtered plurality of portions obtained at act 404. The period may be an average period ($T_{ave}$) and may be calculated in any suitable way, for example, as the average of individual periods ($T_i$) of the n beats included in the arterial waveform. As can be seen in portion 5B-1 of FIG. 5B, each portion has a slightly different duration ($T_i$), as evidenced by the ragged right ends of the waveforms. $T_{ave}$ is the average of these $T_i$ values. The determined average period is used, at acts 408 and 410, to generate, from the filtered portions obtained at act 404, a representative heartbeat waveform having a duration equal to $T_{ave}$. In other embodiments, the median period may be determined and the representative heartbeat waveform generation may have a duration equal to the median period.

Next, at act 408, the filtered portions obtained at act 404 are detrended to obtain a plurality of detrended portions. The detrending is performed to avoid distortion of the waveform as a result of motion artifact, physiologic variation in waveform baseline or amplitude, and remaining beat-to-beat variability in duration. Individual portions may be initially detrended through their original endpoints, at act 408, to account for trends attributable to respiration, fluctuating blood pressure or other artifacts. Beat amplitudes may then be normalized to the overall mean amplitude of the individual beats in order to facilitate signal averaging to be performed at act 410. As a result, all beats will have identical values at the first (fiducial) point and waveform peak.

Subsequently, in some embodiments, further detrending may be performed. For example, in some embodiments, detrending the filtered portions may include detrending filtered portions with periods larger than the average period ($T_{ave}$). All such longer portions are detrended between their foot fiducial point and the point corresponding to the average period. Additionally or alternatively, detrending the filtered portions may include detrending filtered portions with periods smaller than the average period. In some examples, the portions having a period that is less than the average period may be prepared starting from the longest period and proceeded backward to the shortest period. Each such portion may be detrended between the value at their first point and the average value of all longer waveforms at the timepoint equal to the duration of the current portion.

Next, at act 410, process 400 includes averaging the detrended portions obtained at act 408 to obtain the representative heartbeat waveform. The averaging will take into account the number of valid points (beats) at each timestep of the waveform, which will vary in the interval between the duration of the shortest and average duration beats. Panel 5B-3 of FIG. 5B shows an example of a representative heartbeat waveform obtained by detrending and averaging the filtered portions shown in pane 5B-2.

It should be appreciated that process 400 is illustrative and there are variations. For example, in some embodiments, the filtering step may be omitted. As another example, in some embodiments, the detrending step may be omitted.

FIG. 4B is a diagram of an illustrative process 420 for generating a representative heartbeat waveform from an acquired arterial waveform, in accordance with some embodiments of the technology described herein. Process 420 may be performed using any suitable computing device(s). For example, process 420 may be performed by an acquisition device (e.g., acquisition device 120 or 240), a local computing device co-located with the acquisition device (e.g., local computing device 210), or a compute device remote from the acquisition device (e.g., remote computing device 230).

Process 420 begins at act 422, where an acquired arterial waveform is segmented into multiple portions corresponding to multiple respective heartbeats. This may be done in any suitable way including in any of the ways described with respect to act 402 of process 400.

Next, the detected portions may be screened to remove portions exhibiting various artifacts, for example, partial beats, motion artifacts, and irregular heartbeats. To this end, at act 424, the portions may be filtered based on their durations (e.g., as described with reference to act 404 of process 400). At act 426, the portions may be filtered based on their amplitudes (e.g., as described with reference to act 404 of process 400). At act 428, the portions may be filtered based on their shapes (e.g. as described with reference to act 404 of process 400).

Next, at act 430, an average period may be calculated (e.g., as described with reference to act 406 of process 400).

Next, at act 432, the filtered portions may be initially detrended. For example, each of the filtered portions may be initially detrended through their original endpoints to account for trends attributable to respiration, fluctuating blood pressure or other artifacts.

Next, at act 434, the detrended portions may be normalized. For example, amplitudes of each of the filtered portions may be normalized to a mean amplitude of the individual beats in order to facilitate signal averaging. As a result, all portions may have identical or nearly identical values at the first (fiducial) point and waveform peak.

Next, at act 436, the normalized portions with periods larger than the average period may be further detrended. At act 438, the normalized portions with periods smaller than the average period may be further detrended. Details of how this detrending is performed are provided above with reference to act 408 of process 400.

Next, at act 440, the detrended portions are averaged to obtain a representative heartbeat waveform. In some examples, the averaging may account for the number of valid points at each timestep of each portion, which will vary in the interval between the duration of the shortest and average duration portions.

Additional processing may be performed prior to providing a representative heartbeat waveform as input to a machine learning model. For example, the representative heartbeat waveform may be time normalized so that waveforms of a common duration are provided as inputs to the machine learning model (e.g. ML model 730 shown in FIG. 7). In some embodiments, the representative heartbeat waveform may be normalized to have a duration and systolic ejection period similar to the approximate average values for human waveforms taken at rest. For example, the representative heartbeat waveform may be normalized to have a duration of 1000 milliseconds (ms) and a systolic ejection period (SEP) of 320 ms as shown in panel 6-1 of FIG. 6.

Figure 6:
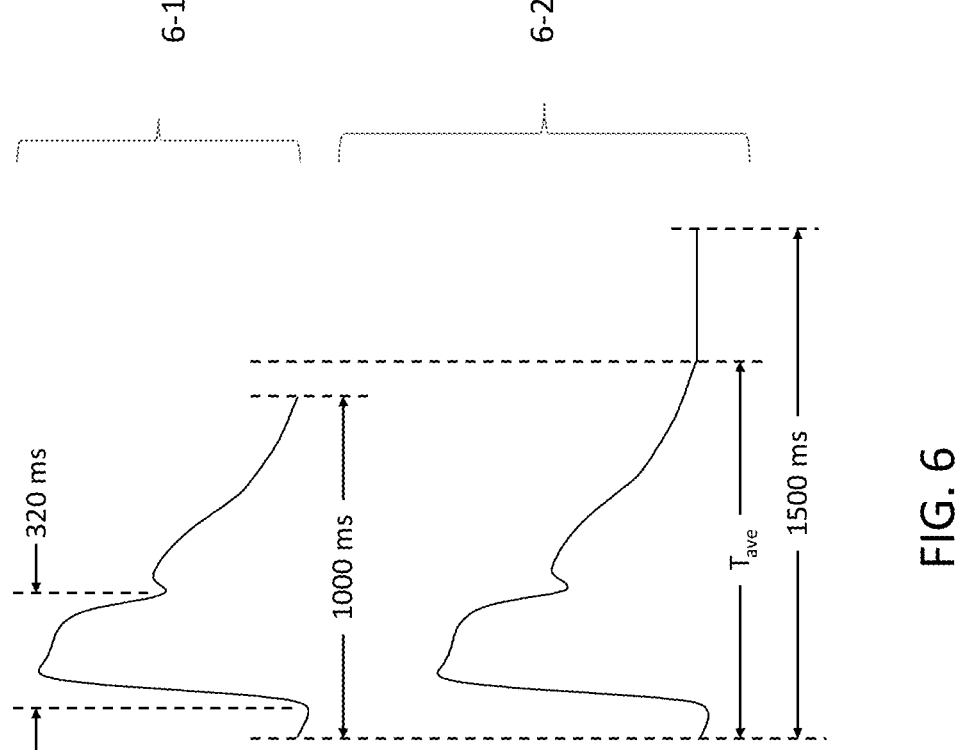
FIG. 6 shows multiple panels including: (i) panel 6-1 which shows an example representative heartbeat waveform that has been normalized, in accordance with some embodiments of the technology described herein; and (ii) panel 6-2 which shows another example of a representative heartbeat waveform that has been normalized, in accordance with some embodiments of the technology described herein.

In some embodiments, the time normalization may be implemented by performing linear interpolation of systole (e.g., to a target duration of 320 ms) followed by linear interpolation of diastole (e.g., to a target duration of 680 ms) as shown in panel 6-1 of FIG. 6. Alternatively, the duration of the representative heartbeat waveform and systolic ejection period may be maintained. In some examples, the representative heartbeat waveform may be padded or truncated to a standard duration. For example, the duration may be of 1000 or 1600 ms or some other suitable value. Panel 6-2 of FIG. 6 shows an example of the representative heartbeat of panel 5B-3 padded to a duration of 1600 ms. In some examples, normalizing the representative heartbeat duration (e.g., to 1000 ms or another value) may be done by simple linear interpolation that maintains the observed relative duration of systole.

In some embodiments, the inputs to machine learning algorithms may be normalized. For example, the representative heartbeat waveform may be initially normalized to a range of 0 to 1 or −1 to 1. As described herein in reference to FIG. 7, inclusion of the first (dP) and second (d2P) derivatives of the representative heartbeat waveform (P) may enhance the ability of the model to accurately predict the value indicative of CFPWV. In some embodiments, the input channels may be standardized by channel (e.g., having mean of 0, standard deviation of 1, for example, by way of Z-score normalization). Alternatively, the 3 input channels can be individually normalized (e.g., having a minimum value of 0, maximum value of 1). Additional transformations can also be used prior to inputting the inputs (e.g., representative heartbeat waveform and/or first and second derivatives) without departing from the spirit of the techniques disclosed herein.

FIG. 7 is an example of a machine learning model 730 for estimating an indication of CFPWV and/or VA, according to some embodiments of the technology described herein. In the illustrated example, the representative heartbeat waveform (in this example the pressure waveform "P"), its derivative waveform (dP) and is second derivative waveform (d2P) may be normalized, as described herein, for example with reference to FIG. 6. The normalized waveforms 710 may be provided as inputs to the machine learning model 730, which is a convolutional neural network (CNN) trained to estimate an indication of CFPWV (e.g., nCFPWV).

It should be appreciated that although in this example embodiment, the pressure waveform and its first two derivatives are provided as inputs to the ML model 730, in other embodiments the pressure waveform with only one derivative (P and dP or P and d2P) may be provided as input to the model 730 or just the pressure waveform P may be provided as input to the model 730 without any derivatives. Additionally, as described herein, in some embodiments, another type of waveform (and, optionally, one or more of its derivatives), for example, an arterial distension or an arterial flow waveform, may be provided as input to ML model 730. In some embodiments, the ML model 730 may take one or more additional inputs including various clinical characteristics, such as chronological age, sex, blood pressure, and measures of additional risk factors.

In some embodiments, including in the example embodiment of FIG. 7, the waveforms 710 may be padded 720 prior to being provided as input. The padding may be zero padding or wrapped padding. However, wrapped padding may be preferable as it maintains the continuous, periodic nature of the input waveform(s).

The padding may be of any suitable length. In some embodiments, the length may be determined, based in part, on the length of the convolutional kernel used as part of the ML model 730. For example, a length 1024 waveform may be padded to up to 1038 points so that a feature map with 1024 points is produced at output of the first convolutional layer 731 since that layer's 15-point convolution kernel results in loss of 7 timesteps on each end of the output waveform. As another example, if an alternative kernel size K is used, the padding layer may be adjusted automatically to pad on each end of the input array by a total of 24 points and an additional number of points equal to the truncated integer value of K/2 points on each end of the input array. This is done to ensure that the average pooling step does not truncate any feature. The padding accounts for half the kernel width on each end.

In some embodiments, including in the example embodiment of FIG. 7, each of the waveforms includes 1024 points. Though in other embodiments, any other suitable length, including by way of example and not limitation, any other suitable length that is a power of two (e.g., 128, 256, 512, 2048, 4096, 8192, etc.) may be used, as aspects of the technology described herein are not limited in this respect. In this example, the duration of 1024 was selected in order to accommodate the series of two-fold reductions in feature space length at the end of each of the eight convolutional layers 731 of the ML model 730 due to averaging average pooling with a stride of 2. The length of the feature map in subsequent layers is preserved by use of zero padding (as opposed to wrapped padding) with an extent equal to half of the convolution kernel width so that as a result, the last convolutional layer of the ML model may output a final flattened array with 1024 features. Other architectures are possible as well.

As shown in FIG. 7, the wrap-padded waveform(s) 720 may be provided as input the machine learning model 730. As shown in FIG. 7, ML model 730 comprises multiple (8 in this example) convolutional blocks, each comprising a convolutional layer 731 (e.g., with a kernel size of 15 and 256 filters), a rectified linear unit (ReLU) layer 732, an average pooling layer 733 (with a stride of 2 in this example), and a dropout layer 734. The output from the last convolutional block is flattened 735 and provided as input to fully connected (or otherwise dense) layer 736 having one output and a linear activation function, which layer outputs an estimated indication of CFPWV 740.

Each convolutional layer 731 in a convolutional block may be a 1-D convolution layer with a given kernel size and filter count. For example, each convolutional layer 731 (e.g., each layer in each of the 8 blocks) may use a kernel size of 15 and 256 filters, although successful usage of alternative or variable values for kernel size and filter count in different convolutional layers 731 (e.g., in different ones of the 8 blocks) is possible.

In the illustrated embodiment, the dropout layer may apply a relative dropout rate of 0.3, which may be useful in that it limits overtraining. However, in other embodiments, other dropout rates may be used, as aspects of the technology described herein are not limited in this respect.

It should be appreciated that the architecture of ML model 730 shown in FIG. 7 is an illustrative example and that other architectures are possible. For example, although in the illustrated embodiment the non-linearity is a ReLU activation function, in other embodiments, a different non-linearity may be used (e.g., sigmoid, hyperbolic tangent, leaky ReLU, etc.), as aspects of the technology described herein are not limited in this respect. As another example, although in the illustrated embodiment, an average pooling layer is used, in other embodiments a max pooling layer may be used and/or the stride may be changed from 2 to any other suitable stride (e.g., 4). As yet another example, in some embodiments, a batch or other type of normalization layer may be added between the convolutional layer 731 and ReLU layer 732. As yet another example, in some embodiments, one or more additional dense layers of various sizes and with various activation functions and levels of dropout can also be placed between the flattened layer 735 and the final linear output layer 736.

The machine learning model 730 may have any number of trainable parameters. For example, the model may have at least one million parameters, at least 5 million parameters, at least 10 million parameters, at least 25 million parameters, between 1 and 10 million parameters (approximately 1, 2, 3, 4, 5, 6, 7, 8, 9, or 10 million parameters), between 5 and 20 million parameters. When trained (using any suitable optimization or other training software, such as the ADAM optimizer, for example) values of these parameters may be estimated from training data.

When training the ML model 730 for a particular application, selection of training data to use for training the model may be used to customize the created model to a particular type of patient. For example, to create ML model 730 for patients having a particular type of medical history (e.g., a history of hypertension or heart failure) training data comprising recorded waveforms (and corresponding measures of CFPWV) for such types of patients may be selected. The ML model 730 may be further customized to a particular individual (e.g., by using data acquired from the particular individual).

Training data may be collected in any suitable manner. For example, in some embodiments, CFPWV and ages of subjects may be collected to train the machine learning model. Subjects may be of a variety of ages and/or ethnic background. The machine learning model may be trained using a normalized CFPWV (e.g., nCFPWV) as the training label (e.g., as it has been shown to relate to abnormalities in and progression of a number of key CVD risk factors, including blood pressure progression and incident hypertension, hyperglycemia, insulin resistance and incident diabetes, and lipid abnormalities). In addition, nCFPWV is a strong predictor of CVD events that has been shown to reclassify risk, especially in younger individuals, in community-based samples.

In some embodiments, the machine learning model may be trained using a variety of waveforms acquired from brachial, radial, femoral and carotid arteries of subjects. The waveforms may be signal averaged (e.g., by using the peak of the R-wave of a simultaneously acquired electrocardiogram as the fiducial point), detrended, normalized, and/or otherwise processed using any of the methods and processes described herein, such as described in reference to FIGS. 4A and 4B. As a result of rescaling, the trained model may be provided with no information regarding calibrated values for blood pressure, heart rate, systolic ejection period or absolute timing of waveform landmarks such as the inflection point marking the return of wave reflections to the proximal aorta. This dual axis standardization of the pressure waveforms forces the model to extract features that depend only on intrinsic waveform shape.

As described above, in some embodiments, subjects may be limited to subjects with one or more shared characteristics, such as age or ethnic background. Measured values for CFPWV may requiring conditioning in order to facilitate and optimize training of the model. For example, values for CFPWV measured in a sample with a broad age range are markedly skewed and heteroskedastic. PWV may represent the distance traveled along an artery, such as the aorta, divided by the transit time. As PWV increases, transit time can become extremely short. Since the transit time is in the denominator, PWV approaches a singularity at high values. Simple inversion of the relation eliminates this singularity and results in a normally distributed value. Since nominal values for CFPWV lie between 3 and 30 m/s, inverse CFPWV can be scaled by −3 to result in normalized CFPWV (nCFPWV=−3/CFPWV), which is a well-behaved, normally distributed variable that ranges from −1.0 to −0.1.

As has been described above, a representative heartbeat waveform is provided as input to a trained machine learning model (e.g., the model shown in FIG. 7) and the representative heartbeat waveform is obtained, in part, by averaging portions of the arterial waveform corresponding to respective heartbeats. In other embodiments, instead of segmenting the arterial waveform into portions and averaging them, the arterial waveform may be provided directly as input to an ML model. For example, an acquisition of 8192 raw points may be provided as input to the model, (this would encompass approximately 8 of the heartbeats shown in FIG. 5A assuming a sample rate of 1000 Hz). Alternatively, 1024 points could be used at a sample rate of 125 Hz (which is a more typical sample rate for a smart watch PPG sensor or smart phone camera) and still provide about 8 beats to the model. This "full waveform" approach may also perform well, but may be less computationally efficient than the signal averaging approach described herein.

Additional Implementation Detail

Figure 8:
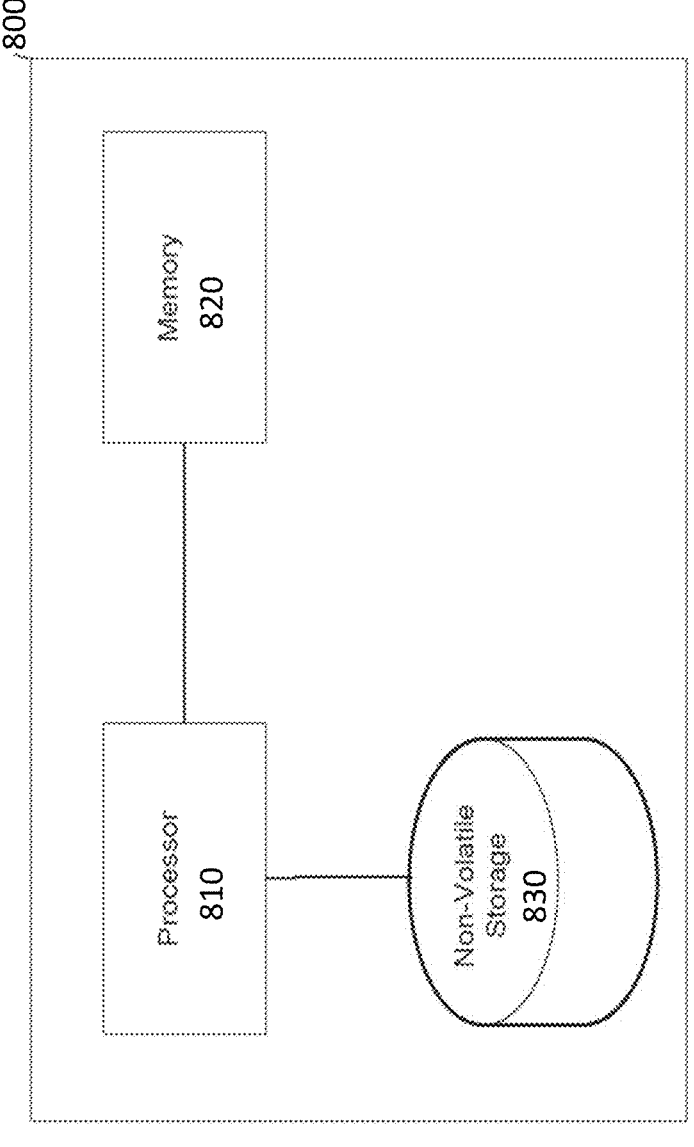
FIG. 8 is a block diagram of an illustrative computer system that may be used in implementing some embodiments of the technology described herein.

An illustrative implementation of a computer system 800 that may be used in connection with any of the embodiments of the disclosure provided herein is shown in FIG. 8. The computer system 800 may include one or more processors 810 and one or more articles of manufacture that comprise non-transitory computer-readable storage media (e.g., memory 820 and one or more non-volatile storage media 830). The processor(s) 810 may control writing data to and reading data from the memory 820 and the non-volatile storage device 830 in any suitable manner, as the aspects of the technology described herein are not limited in this respect. To perform any of the functionality described herein, the processor(s) 810 may execute one or more processor-executable instructions stored in one or more non-transitory computer-readable storage media (e.g., the memory 820), which may serve as non-transitory computer-readable storage media storing processor-executable instructions for execution by the processor(s) 810.

The terms "program" or "software" are used herein in a generic sense to refer to any type of computer code or set of processor-executable instructions that can be employed to program a computer or other processor to implement various aspects of embodiments as described herein. Additionally, in some embodiments, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have attributes that are related through location in the data structure. Such relationships may likewise be achieved by assigning storage for the attributes with locations in a non-transitory computer-readable medium that convey relationship between the attributes. However, any suitable mechanism may be used to establish relationships among information in attributes of a data structure, including through the use of pointers, tags or other mechanisms that establish relationships among data elements.

Also, various inventive concepts may be embodied as one or more processes. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as terms to distinguish one claim element having a certain name from another element having a same name (but for use of the ordinal term).

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "substantially," "approximately," and "about" may be used to mean within ±20% of a target value in some embodiments, within ±10% of a target value in some embodiments, within ±5% of a target value in some embodiments, within ±2% of a target value in some embodiments. The terms "approximately" and "about" may include the target value.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A method for using a machine learning model to estimate an indication of carotid-femoral pulse wave velocity (CFPWV) and/or vascular age (VA) of a subject from an arterial waveform previously measured at a single site by an arterial waveform acquisition device coupled to the subject, the method comprising:

using at least one computer hardware processor to perform:

obtaining the arterial waveform, the arterial waveform comprising a plurality of portions corresponding to a respective plurality of heartbeats of the subject, the plurality of portions comprising at least 10 portions, each of the plurality of portions comprising at least 250 data points;

generating a representative heartbeat waveform from the arterial waveform, the generating comprising:

detecting the plurality of portions in the arterial waveform;

individually detrending each of the detected plurality of portions to obtain a plurality of detrended portions, averaging portions in the plurality of detrended portions to obtain the representative heartbeat waveform; and processing the representative heartbeat waveform and at least one derivative waveform of the representative heartbeat waveform using a trained one-dimensional (1D) convolutional neural network (CNN) model to produce a corresponding output indicative of the CFPWV of the subject, wherein the 1D CNN comprises multiple 1D convolutional layers, multiple rectified linear unit layers, multiple pooling layers, and a fully-connected layer, wherein the 1D CNN comprises at least one million parameters, and wherein the processing comprises calculating the output indicative of the CFPWV from the representative heartbeat waveform the at least one derivative waveform and the at least one million parameters.

2. The method of claim 1, wherein the arterial waveform acquisition device comprises a tonometer, a plethysmographic (PG) device, an echocardiographic device, a digital blood pressure system, an electrical impedance sensor, and/or an ultrasound imaging device.

3. The method of claim 1, wherein the arterial waveform acquisition device comprises a wearable device.

4. The method of claim 1, wherein the arterial waveform comprises a pressure waveform or an arterial distension waveform.

5. The method of claim 1, wherein the arterial waveform comprises an arterial flow waveform.

6. The method of claim 1, wherein the plurality of portions comprises at least 100 portions corresponding to a respective plurality of heart beats.

7. The method of claim 1, wherein each portion of the plurality of portions comprises at least 500 data points.

8. The method of claim 1, further comprising:

removing one or more portions from the detected plurality of portions prior to performing the detrending.

9. The method of claim 1, wherein generating the heartbeat waveform from the arterial waveform comprises:

after detecting the plurality of portions in the arterial waveform, removing one or more portions from the detected plurality of portions to obtain a filtered plurality of portions; and determining a period for the filtered plurality of portions, wherein the individually detrending is performed on at least some of the filtered plurality of portions and based on the determined period to obtain the plurality of detrended portions.

10. The method of claim 1, further comprising:

predicting vascular age (VA) of the subject using a linear regression model different from the trained machine learning model and the output indicative of the CFPWV of the subject.

11. The method of claim 1, further comprising:

predicting aortic stiffness of the subject using the output indicative of the CFPWV of the subject.

12. The method of claim 1, further comprising:

predicting risk of the subject for developing any of hypertension, diabetes, obesity, myocardial infarction, heart failure, stroke, kidney disease, cognitive impairment and dementia using the output indicative of the CFPWV of the subject.

13. The method of claim 1, wherein the corresponding output indicative of the CFPWV of the subject indicates normalized CFPWV (nCFPWV).

14. A system, comprising:

at least one computer hardware processor; and at least one non-transitory computer-readable storage medium storing processor-executable instructions that, when executed by the at least one computer hardware processor, cause the at least one computer hardware processor to perform a method for using a machine learning model to estimate an indication of carotid-femoral pulse wave velocity (CFPWV) and/or vascular age (VA) of a subject from an arterial waveform previously measured at a single site by an arterial waveform acquisition device coupled to the subject, the method comprising:

obtaining the arterial waveform, the arterial waveform comprising a plurality of portions corresponding to a respective plurality of heartbeats of the subject, the plurality of portions comprising at least 10 portions, each of the plurality of portions comprising at least 250 data points;

generating a representative heartbeat waveform from the arterial waveform, the generating comprising:

detecting the plurality of portions in the arterial waveform;

individually detrending each of the detected plurality of portions to obtain a plurality of detrended portions, averaging portions in the plurality of detrended portions to obtain the representative heartbeat waveform; and processing the representative heartbeat waveform and at least one derivative waveform of the representative heartbeat waveform using a trained one-dimensional (1D) convolutional neural network (CNN) model to produce a corresponding output indicative of the CFPWV of the subject, wherein the 1D CNN comprises multiple 1D convolutional layers, multiple rectified linear unit layers, multiple pooling layers, and a fully-connected layer, wherein the 1D CNN comprises at least one million parameters, and wherein the processing comprises calculating the output indicative of the CFPWV from the representative heartbeat waveform the at least one derivative waveform and the at least one million parameters.

15. The system of claim 14, wherein the corresponding output indicative of the CFPWV of the subject indicates normalized CFPWV (nCFPWV).

16. The system of claim 14, wherein the plurality of portions comprises at least 100 portions corresponding to a respective plurality of heart beats, and wherein each portion of the plurality of portions comprises at least 500 data points.

17. The system of claim 14, wherein the method further comprises:

predicting vascular age (VA) of the subject using a linear regression model different from the trained machine learning model and the output indicative of the CFPWV of the subject; and/or predicting aortic stiffness of the subject using the output indicative of the CFPWV of the subject.

18. At least one non-transitory computer readable storage medium storing processor-executable instructions that, when executed by at least one computer hardware processor, cause the at least one computer hardware processor to perform a method for using a machine learning model to estimate an indication of carotid-femoral pulse wave velocity (CFPWV) and/or vascular age (VA) of a subject from an arterial waveform previously measured at a single site by an arterial waveform acquisition device coupled to the subject, the method comprising:

obtaining the arterial waveform, the arterial waveform comprising a plurality of portions corresponding to a respective plurality of heartbeats of the subject, the plurality of portions comprising at least 10 portions, each of the plurality of portions comprising at least 250 data points;

generating a representative heartbeat waveform from the arterial waveform, the generating comprising:

detecting the plurality of portions in the arterial waveform;

individually detrending each of the detected plurality of portions to obtain a plurality of detrended portions, averaging portions in the plurality of detrended portions to obtain the representative heartbeat waveform; and processing the representative heartbeat waveform and at least one derivative waveform of the representative heartbeat waveform using a trained one-dimensional (1D) convolutional neural network (CNN) model to produce a corresponding output indicative of the CFPWV of the subject, wherein the 1D CNN comprises multiple 1D convolutional layers, multiple rectified linear unit layers, multiple pooling layers, and a fully-connected layer, wherein the 1D CNN comprises at least one million parameters, and wherein the processing comprises calculating the output indicative of the CFPWV from the representative heartbeat waveform the at least one derivative waveform and the at least one million parameters.

19. The at least one non-transitory computer readable storage medium of claim 18, wherein the plurality of portions comprises at least 100 portions corresponding to a respective plurality of heart beats, and wherein each portion of the plurality of portions comprises at least 500 data points.

20. The at least one non-transitory computer readable storage medium of claim 18, wherein the method further comprises:

predicting vascular age (VA) of the subject using a linear regression model different from the trained machine learning model and the output indicative of the CFPWV of the subject; and/or predicting aortic stiffness of the subject using the output indicative of the CFPWV of the subject.

* * * * *